US008251940B2

(12) United States Patent
Harris, Jr. et al.

(10) Patent No.: US 8,251,940 B2
(45) Date of Patent: Aug. 28, 2012

(54) VIBRATION DAMPENING DEVICE AND METHOD

(76) Inventors: Charles Harris, Jr., New Castle, DE (US); John Garnier, Newark, DE (US)

( * ) Notice: Subject to any disclaimer, the term of this patent is extended or adjusted under 35 U.S.C. 154(b) by 837 days.

(21) Appl. No.: 10/709,903

(22) Filed: Jun. 4, 2004

(65) Prior Publication Data

US 2005/0273029 A1     Dec. 8, 2005

(51) Int. Cl.
*A61F 13/00*     (2006.01)
*A61F 13/06*     (2006.01)
*A61F 15/00*     (2006.01)

(52) U.S. Cl. ........... 602/60; 602/41; 602/42; 602/43; 602/52; 602/53; 602/54; 602/58; 602/78; 128/888; 128/889; 128/893; 128/894

(58) Field of Classification Search ........... 602/41–43, 602/58, 60, 78, 52–54; 128/888–889, 893–894
See application file for complete search history.

(56) References Cited

U.S. PATENT DOCUMENTS

| | | | |
|---|---|---|---|
| 2,998,008 A * | 8/1961 | Klesa | 128/878 |
| 4,014,327 A | 3/1977 | Spiro | |
| 5,338,290 A | 8/1994 | Aboud | |
| 5,478,306 A | 12/1995 | Stoner | |
| 5,865,775 A | 2/1999 | Peoples et al. | |
| 5,901,379 A | 5/1999 | Hirata | |
| 5,921,949 A * | 7/1999 | Dray | 602/64 |
| 5,971,947 A | 10/1999 | McNally et al. | |
| 6,120,472 A | 9/2000 | Singer, Jr. | |
| 6,149,617 A | 11/2000 | McNally et al. | |
| 6,149,618 A | 11/2000 | Sato | |
| 6,155,999 A * | 12/2000 | Bartlett | 602/60 |
| 6,213,969 B1 | 4/2001 | MacMorran et al. | |
| 6,217,536 B1 * | 4/2001 | Gustafson | 602/21 |
| 6,315,748 B1 * | 11/2001 | Morgan, Jr. | 602/21 |
| 6,361,549 B1 | 3/2002 | Asatourian et al. | |
| 6,478,760 B2 | 11/2002 | Darcey | |
| 6,517,507 B1 | 2/2003 | Faherty | |
| 6,565,524 B1 | 5/2003 | Itonaga et al. | |
| 6,576,808 B1 * | 6/2003 | Dreyer | 602/42 |
| 6,582,449 B2 | 6/2003 | Grey et al. | |
| 6,585,674 B2 | 7/2003 | Toda | |
| 6,790,520 B1 * | 9/2004 | Todd et al. | 428/318.4 |
| 7,207,962 B2 * | 4/2007 | Anand et al. | 602/8 |
| 7,361,154 B2 * | 4/2008 | Jablonka et al. | 602/20 |

* cited by examiner

*Primary Examiner* — Patricia Bianco
*Assistant Examiner* — Brandon L Jackson
(74) *Attorney, Agent, or Firm* — Patricia S. Rogowski; Donald W. Huntley; Jeffrey R. Ramberg

(57) ABSTRACT

A vibration dampening device is a patch with one or more step members that have distal ends extending from the patch. The patch is removably engaged or adhered to a wearer's skin. With the patch engaged, the distal ends of the step members have freedom of movement with respect to the patch. The patch optionally may further include one or more wing sections integrally formed therein that also have freedom of movement with respect to the portion of the patch engaged or adhered to skin. Step member and/or wing section movement counteracts longitudinal and/or radial vibrations traveling through soft tissue and musculature to dampen such vibrations.

19 Claims, 2 Drawing Sheets

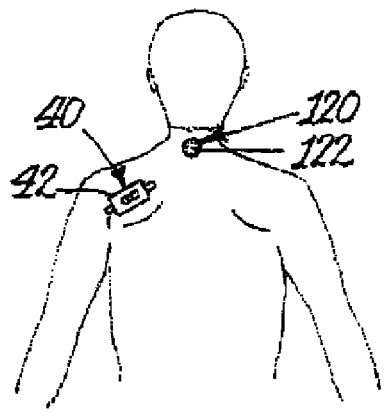
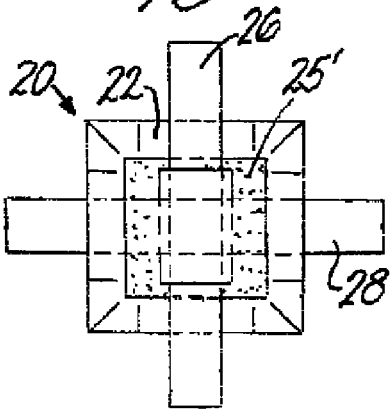
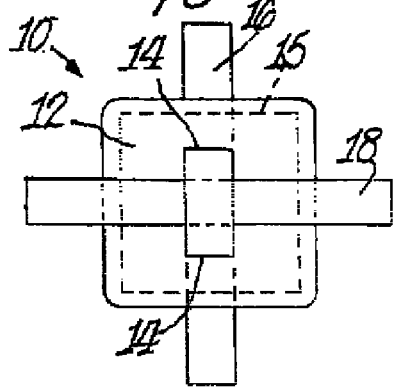
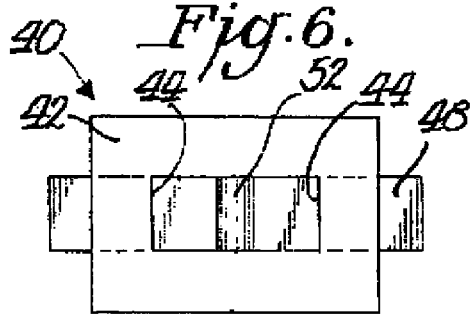
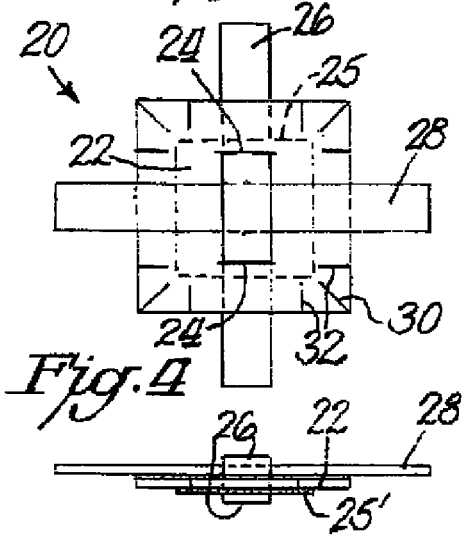
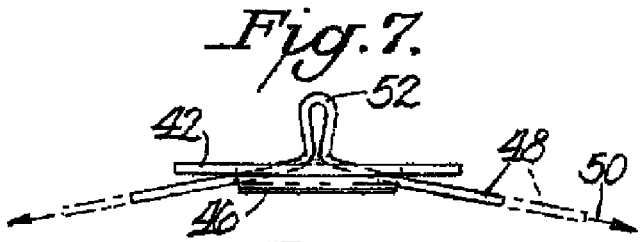
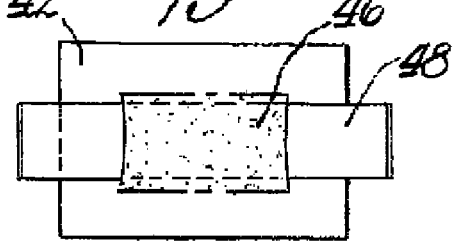
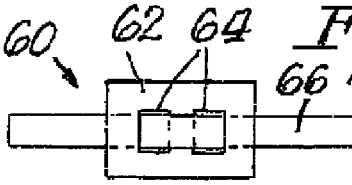

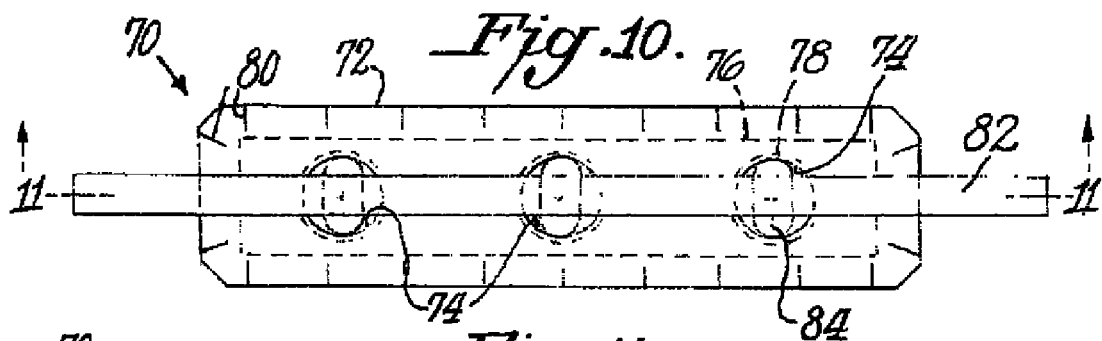
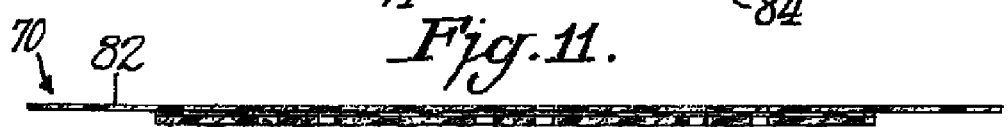
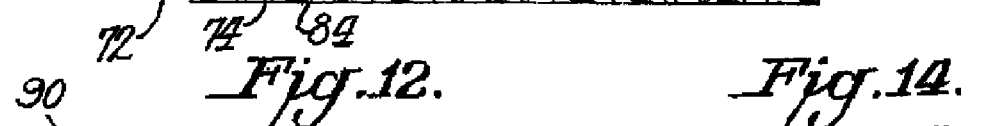
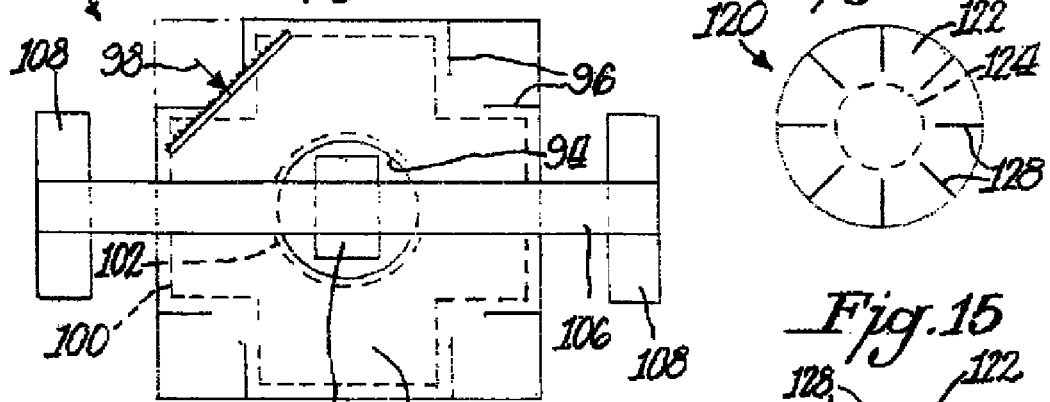
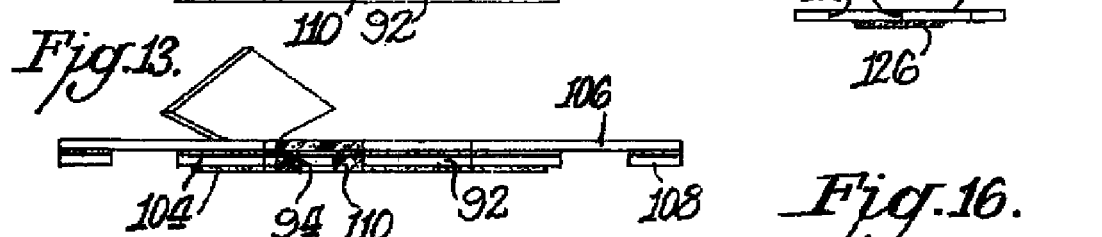
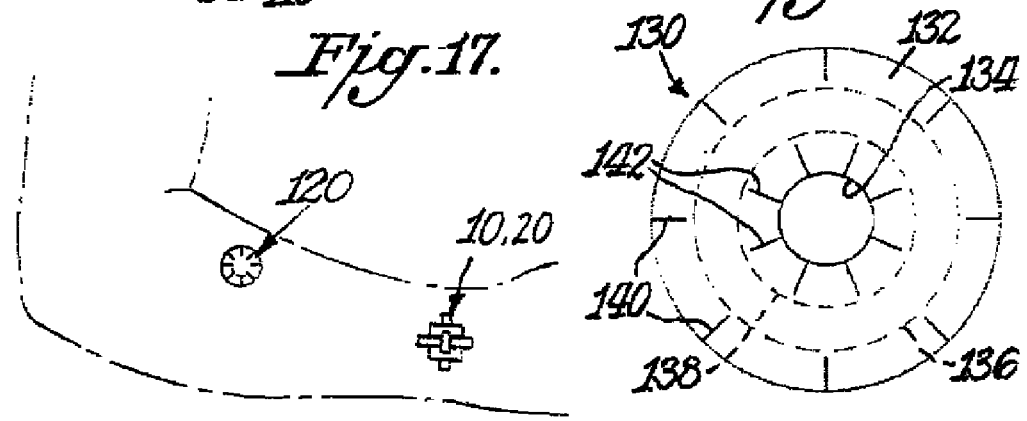

VIBRATION DAMPENING DEVICE AND METHOD

FIELD OF THE INVENTION

The present invention relates to a vibration dampening patch that is removably engaged to a person's body to dampen vibration of nearby musculature and soft tissue thereby preventing possible injury or pain that would otherwise result from repeated muscle and soft tissue vibration.

BACKGROUND OF THE INVENTION

Impact-induced vibrations that travel along a human body part, such as a tendon or ligament, may lead to muscle or joint fatigue, or even injury. For example, a vibrating tennis racket held in the hand will transmit longitudinally and radially traveling vibrations into the hand, wrist, elbow, upper arm and shoulder. For some, these repeated vibrations lead to a painful injury termed "tennis elbow".

Several methods for isolating or reducing vibrations are discussed in the prior art. For example, a dampening device containing one or more springs may be attached directly to racket strings to try to dampen string-induced vibrations before the vibrations reach the racket handle. While effective to some degree, such devices do not completely eliminate vibrations from being transmitted to the hand, wrist, forearm, elbow, etc.

An alternative vibration reducing method is to apply a vibration absorber to the vibration source (sometimes termed an "active" or "dynamic" vibration absorber). Dynamic vibration absorbers use a mass-spring combination that can be tuned to exert a force equal and opposite to a sensed vibration. Dynamic vibration absorbers require an electronic power source and are not considered practical for use in racket sports.

Yet another alternative is a "passive" vibration absorber, which incorporates mechanical means such as a mass-spring-fluid combination, to dampen excessive unwanted vibrations. To be effective, passive vibration absorbers require a means to apply a counter force to a vibration, such as with automobile shock absorbers that have a spring, a piston and fluid forced by the piston from one chamber into another chamber.

A number of supports and braces have been proposed for use to treat "tennis elbow" and other impact-induced shock on the human elbow joint. For example, U.S. Pat. No. 5,865,775 discloses a forearm sleeve 10 with an energy-attenuating viscoelastic means 50 affixed to such sleeve. A tension strap 32 is wrapped around the sleeve to counter forces directed radially outwardly from the sleeve and the viscoelastic means 50. Such sleeve and band combination purports to dampen vibrations emanating radially outwardly from the bone to the outer skin of the arm, but has no effect on vibrations of soft tissue, particularly vibrations emanating longitudinally or along the length of the arm.

U.S. Pat. No. 6,149,617 discloses a tennis elbow band that incorporates a removable thermal packet 20 therein. The thermal packet may be heated or chilled before it is inserted into the band. The band with thermal packet therein is tightened around a wearer's forearm to apply pressure and may be in combination with heating or cooling (if the thermal packet has been heated or chilled). The band has no effect on minimizing or dampening vibrations of soft tissue which travel in a longitudinal direction along a wearer's arm.

U.S. Pat. No. 5,338,290 shows a variable tension band formed as a laminate with multiple strips of elastic material 11 attached to one another with reinforcing ribs 13. The band is wrapped around a body part with sufficient tension to relieve pain. The ends of the band are joined together with hook and loop fasteners 12a, 12b. The patent indicates that joint pain may be relieved by wrapping the band around a body part at least one inch away from the joint. The band has no effect on vibrations which travel in a longitudinal direction along a wearer's arm or along a wearer's leg.

Bands have also been proposed for wrapping about the wrist to support the carpals and aid in preventing or treating carpal tunnel syndrome. See, e.g. U.S. Pat. Nos. 5,478,306 and 6,517,507. Such bands tightly encircle the wrist, but have no means for dampening vibrations of soft tissue which travel in a longitudinal direction from the hand across the wrist and along the wearer's arm.

U.S. Pat. No. 5,921,949 discloses a carpal tunnel wrist corrective support formed as a flexible strap with an inner surface onto which at least two compression pads are removably applied. The compression pads 41 and 42 are shown aligned with their major axis perpendicular to the longitudinal axis of the strap. The compression pads are fully adhered to the inner surface with hook and loop fasteners provided over the entire pad surface. There is no portion of a compression pad extending outwardly from the edges of the strap or left to freely vibrate without connection to the strap. Hence the strap has no means for dampening vibrations of soft tissue which travel in a longitudinal direction from the hand across the wrist and along the wearer's arm.

U.S. Pat. No. 6,585,674 shows a stretchable band having a wedge-shaped foam piece 14 adhered to one surface. The wedge-shaped foam piece supports a wearer's foot while the band is wrapped around the wearer's ankle. The band and wedge are intended to better align a wearer's foot and ankle to minimize injury to the knee. No means are provided for dampening vibrations of soft tissue which travel in a longitudinal direction from the foot across the ankle and along the wearer's leg.

Effective means for isolating and/or reducing impact-induced vibrations from traveling longitudinally along soft tissue of human extremities are still sought.

SUMMARY OF THE INVENTION

In a first aspect of the invention, a vibration dampening device that may be engaged to human skin is a patch having a nominal width and a nominal length and defining an outer periphery, wherein the patch has a body contacting surface and an outer surface. The patch has a central portion to which a pressure sensitive adhesive may be applied on the body-contacting surface. Alternatively, the patch may be engaged to or formed within a suspending strap.

One or more step members are engaged to the patch. Each step member has a distal end that extends beyond the outer periphery of the patch and has freedom of movement with respect to the patch. Preferably, each step member has two ends and both ends extend beyond the outer periphery of the patch.

The step member preferably is made from a viscoelastic material having a density in the range of 7 to 15 pounds per cubic foot, a tensile strength from 40 to 80 psi and a minimum elongation of 100%. Most preferably, the viscoelastic material has a compression deflection at 25% of from 3 to 10 psi.

Preferably, the patch defines a slot and at least one step member is engaged to the patch by threading it through the slot. The patch may define more than one slot, such that the step member is threaded through multiple slots. In one embodiment with two slots, a step member is slidably engaged to the patch such that the distal end and the other end of such step member are adjustably extended away from the outer periphery of the patch by sliding the step member within the first slot and the second slot.

In one embodiment, the step members are engaged or attached to the outer surface of the patch, but the distal ends of such step members extend beyond the outer periphery of the patch and have freedom of movement with respect to the patch. It is possible for the step members to be configured so that their central longitudinal axes are oriented perpendicularly.

In another embodiment, the patch further comprises one or more wings formed in the outer periphery of the patch. Such wings may be formed by slitting through a portion of the patch, such as forming slits through the periphery of the patch without cutting into a central portion. Wings formed between the slits have freedom of movement with respect to the central portion. If adhesive is used to engage the patch to the wearer's skin, adhesive is applied on the body contacting surface at the central portion of the patch so that the wings retain freedom of movement with respect to the central portion. The body contacting surface of the patch at the central portion is constrained from movement with respect to the skin to which the patch is engaged.

Extensions may be appended to the distal end of the step member(s) to vary the dampening response of the step members to vibrations. In one embodiment, an extension has two ends and defines an axis along its length, and is appended to the distal end of the step member such that the axis of the extension is substantially perpendicular to the center axis of the step member. In this embodiment, the ends of the extension preferably extend beyond the width of the step member.

Alternatively, extensions may be applied to the step member(s) along their length. In such embodiments, preferably, the patch defines a central opening formed therethrough, and an extension is appended to the step member at a position along its length to correspond to the position of the central opening in the patch so that the extension is held within the central opening formed through the patch. Extensions have a body contacting surface and may be formed to have a simple geometric shape selected from the group consisting of: square, rectangle, triangle, oval, and circle.

A further embodiment of a vibration dampening device according to the invention is a patch defining an outer periphery and a central portion, wherein said patch has a body contacting surface and an outer surface, and wherein at the central portion the body contacting surface is constrained from movement relative to the skin to which the patch is engaged. One or more wings are formed in the outer periphery of the patch, and such wings do have freedom of movement relative to the central portion of the patch. Preferably, such wings are formed by slitting through a portion of the patch, such as by forming a series of slits cut through the patch at its outer periphery. The patch may be formed to have any shape, such as but not limited to, a simple geometric shape selected from the group consisting of: square, rectangle, triangle, oval, and circle. The patch may be engaged to a wearer's skin with a pressure sensitive adhesive that is applied to the body contacting surface of the patch at the central portion.

In one embodiment, the patch further defines an opening formed therethrough at the central portion of the patch. In this embodiment, second wings are formed by slitting through a portion of the patch at the central opening.

The invention further comprises method for dampening vibration of soft tissue or musculature of a human wearer's body part by removably engaging a vibration dampening device to the body part. The vibration dampening devices may be one or a combination of the devices described.

BRIEF DESCRIPTION OF THE DRAWINGS

FIG. 1 is a fragmental rear elevational view of an adult male showing his head, neck, back, shoulders and arms, and having two embodiments of vibration dampening patches according to the invention applied at the base of the neck and at one shoulder blade;

FIG. 2 is a top plan view of a first embodiment of a vibration dampening patch according to the invention;

FIG. 3 is a top plan view of a second embodiment of a vibration dampening patch according to the invention;

FIG. 4 is a side elevational view of the patch of FIG. 3;

FIG. 5 is a bottom plan view of the patch of FIGS. 3 and 4;

FIG. 6 is a top plan view of a third embodiment of a vibration dampening patch according to the invention;

FIG. 7 is a side elevational view of the patch of FIG. 6;

FIG. 8 is a bottom plan view of the patch of FIGS. 6 and 7;

FIG. 9 is a top plan view of a fourth embodiment of a vibration dampening patch according to the invention;

FIG. 10 is a top plan view of a fifth embodiment of a vibration dampening patch according to the invention;

FIG. 11 is a cross-sectional view in elevation taken along line 11-11 of FIG. 10;

FIG. 12 is a top plan view of a sixth embodiment of a vibration dampening patch according to the invention;

FIG. 13 is a side elevational view of the patch of FIG. 12, having a portion broken away to show the laminate structure of the patch;

FIG. 14 is a top plan view of a seventh embodiment of a vibration dampening patch according to the invention;

FIG. 15 is a side elevational view of the patch of FIG. 14;

FIG. 16 is a top plan view of an eighth embodiment of a vibration dampening patch according to the invention; and FIG. 17 is a schematic diagram of a wearer's arm to which vibration dampening patches of the second and seventh embodiments have been applied.

DESCRIPTION OF THE PREFERRED EMBODIMENTS

Referring first to FIG. 2, a first embodiment of a vibration dampening device 10 has a patch 12 that defines an outer periphery and two slots 14. The patch 12 further has a skin-contacting surface and an outer surface. As shown in FIG. 2, the patch 12 has a generally square shape in plan view, although other regular and irregular patch shapes are contemplated in this invention, such as but not limited to round, oval, triangular and circular.

Dotted line 15 encompasses the region on the skin-contacting surface of the patch 12 to which an adhesive is applied. A pressure sensitive adhesive, such as Part #1524 by Minnesota Mining and Manufacturing (3M), is one type of adhesive that may be applied. The patch is intended for removable engagement to a wearer's skin, so the adhesive selected for the skin-contacting surface of the patch 12 preferably should permit comfortable engagement to and removal from skin.

A first step member 16 is threaded through the slots 14, so that a central portion of such step member 16 contacts the outer surface of the patch 12 while the ends of the step member 16 extend beyond the periphery of the patch 12. The first step member 16 may be held in position where portions contact the adhesive on the skin-contacting surface of the patch 12. The ends of the first step member 16 have freedom of movement with respect to the patch 12.

Preferably, as shown in FIG. 2, a second step member 18 is threaded under the central portion of the first step member, and is in contact with the first step member and the outer surface of the patch 12. The ends of the second step member shown in FIG. 2 extend beyond the outer periphery of the patch 12. The ends of the second step member 18 have freedom of movement with respect to the patch 12.

Although the patch 12 is engaged to the wearer's skin with a pressure sensitive adhesive, alternative engagement means are within the scope of the present invention. For example, the patch 12 could be mounted onto a suspender such that the skin-contacting surface of the patch is in contact with the wearer's skin. The step members 16 and 18 still have ends that extend beyond the outer periphery of the patch 12 and have freedom of movement with respect to the patch whether the patch 12 is engaged using an adhesive or using an alternate engagement means.

Referring next to FIGS. 3 to 5, a second embodiment 20 of a vibration dampening device has a patch 22 that defines an outer periphery and two slots 24. The patch 22 further has a skin-contacting surface and an outer surface. As shown in FIG. 3, the patch 22 has a generally square shape in plan view, although other regular and irregular patch shapes are contemplated in this invention. Dotted line 25 encompasses the region on the skin-contacting surface of the patch 22 to which an adhesive 25' is applied. As with the first embodiment, the patch 22 of the second embodiment 20 is intended for removable engagement to a wearer's skin, so the adhesive selected preferably should permit comfortable engagement to and removal from skin. A pressure sensitive adhesive is one type of adhesive that may be applied.

A first step member 26 is threaded through the slots 24, so that a central portion of such step member 26 contacts the outer surface of the patch 22 while the ends of the step member 26 extend beyond the periphery of the patch 22. The first step member 26 may be held in position where portions contact the adhesive on the skin-contacting surface of the patch 22. The ends of the first step member 26 have freedom of movement with respect to the patch 22.

Preferably, as shown in FIGS. 3 to 5, a second step member 28 is threaded under the central portion of the first step member, and is in contact with the first step member 26 and the outer surface of the patch 22. The ends of the second step member 28 shown in FIG. 3 extend beyond the outer periphery of the patch 22. The ends of the second step member 28 have freedom of movement with respect to the patch 22.

Different from the first embodiment 10 shown in FIG. 2, the second embodiment 20 shown in FIGS. 3 to 5 further comprises wing sections at the outer periphery of the patch 22. The wing sections are formed by cutting slits 30 diagonally from the corners of the patch 22, and by cutting slits 32 adjacent to, but separated from, the diagonal slits 30. The series of slits 30, 32 at each corner of the patch 22 allows peripheral portions of the patch material to have freedom of movement with respect to the central portion of the patch to which adhesive 25' is applied.

Referring next to FIGS. 6 to 8, a third embodiment 40 of the vibration dampening device according to the invention has a patch 42 defining an outer periphery and two slots 44 therein. The patch 40 has a skin-contacting surface and an outer surface. Adhesive 46 suitable for skin contact is applied to a portion of the skin-contacting surface. Preferably, adhesive 46 is applied to the portion of the skin-contacting surface between the slots 44.

A step member 48 is threaded through the slots 44, so that a central portion of such step member 48 contacts the outer surface of the patch 42 while the ends of the step member 48 extend beyond the periphery of the patch 42. The ends of the step member 48 have freedom of movement with respect to the patch 40. In this embodiment 40, the step member 48 is movably engageable within the slots 44 such that the ends of the step member 48 may be pulled further outwardly from the slots 44. As shown in FIG. 7, arrows 50 show the direction of movement of the ends of the step member 48 to adjust the extent to which the ends of the step member 48 extend beyond the patch 42. The center portion of step member 48 is formed into a loop 52 when the step member has not been extended outwardly to its full length. The step member 48 thus may be adjusted to have a greater or lesser portion of each end extended beyond the periphery of the patch 42. The step member 48 may be so adjusted even when the patch 42 is engaged or adhered to a wearer's skin.

Referring next to FIG. 9, a fourth embodiment of a vibration dampening device 60 is a patch 62 that defines an outer periphery and a skin-contacting surface and an outer surface. The patch 62 as shown in FIG. 9 has a generally rectangular shape in top plan view, although other shapes are contemplated and within the scope of this invention. The patch 62 further defines a series of slots 64 therethrough. Slots 64 are spaced apart from one another and preferably are formed by cutting material out of the patch 62. Adhesive (not shown) is applied to or found on at least a portion of the skin-contacting surface of the patch 62 so that the patch 62 may be engaged or adhered to a wearer's skin.

A step member 66 is threaded through slots 64. As shown in FIG. 9, step member 66 has two ends, each of which extends beyond the outer periphery of the patch 62. The fourth embodiment 60 shows the central axis of the step member 66 generally aligned with the central axis of the patch 62, although other orientations are possible and contemplated within this invention. The ends of the step member 66 have freedom of movement with respect to the patch 62. Moreover, comparable to the third embodiment 40, the extent to which the ends of the step member 66 extend beyond the periphery of the patch 62 can be varied by sliding the step member 66 within the slots 64.

FIGS. 10 and 11 show a fifth embodiment 70 of a vibration dampening device of the invention in which a patch 72 has an elongate shape in plan view and defines a skin-contacting surface and an outer surface. The patch of FIG. 10 in plan view has a generally rectangular shape with cropped corners, although other shapes are contemplated and are within the scope of this invention. A series of three round holes 74 are formed through the thickness of the patch 72. The dotted lines 76, 78 bound the region to which adhesive is applied on the skin-contacting surface of the patch 72. Slits 80 are cut through the thickness of the material forming the patch 72 to create wing sections at the patch outer periphery. The wing sections comprise outer portions of the patch that do not have adhesive applied to the skin contacting surface. Thus, the wing sections have some freedom of movement with respect to the central portion of the patch 72.

A step member 82 is engaged or adhered to the outer surface of the patch 72. The step member 82 defines a first surface, an outer surface and two ends. As shown in FIG. 10, the ends of the step member 82 extend beyond the outer periphery of the patch 72. Portions of the first surface of the step member 82 are attached to the outer surface of the patch 72. Extension members 84 are attached to portions of the first surface of the step member 82. The extension members 84 have generally oval shapes with their ends extending beyond the width of the step member 82. Alternate shapes are possible for the extension members. The extension members 84 are positioned to fit within the holes 74 in the patch 72. As shown in FIG. 10, an extension member 84 is positioned within each hole 74 in the patch 72. The extension members 84 have freedom of movement with respect to the patch 72, and thus may contact the wearer's skin through the holes in the patch 72. Preferably, no adhesive is applied to the skin-contacting surface of the extension members 84 to allow the freedom of movement with respect to the patch 72. Thus, when the skin-contacting surface of the patch 72 is engaged or adhered to a wearer's skin, the ends of the step member 82 and the extension members 84 still have freedom of movement with respect to the patch 72 so as to help dampen vibrations traveling along the skin and soft muscle tissue.

Referring next to FIGS. 12 and 13, a sixth embodiment 90 of a vibration dampening device according to the invention is a patch 92 defining an outer periphery and a skin-contacting surface and an outer surface. The patch 92 shown in FIG. 12 has a generally square shape in plan view, although other shapes are contemplated within the invention. The patch 92 further defines a central hole 94 therethrough. The hole 94 is shown as generally circular, although other shapes are contemplated within the invention. Slits 96 are cut through the thickness of the patch 92 adjacent to the corners of the patch 92. By forming slits 96 in the patch 92, the corner portions of the patch form wing sections that have freedom of movement with respect to the central portion of the patch 92. As shown in FIG. 12, for purposes of illustration, one of the wing sections has been folded upwardly at arrow 98. In use, the wing section generally would not be folded upwardly. Dotted lines 100, 102 define the boundaries within which adhesive 104 may be applied to the skin-contacting surface of the patch 92.

Step member 106 has a top surface, a bottom surface and two ends. The bottom surface of the step member 106 is engaged or adhered to the outer surface of the patch 92 at points of contact. The ends of step member 106 extend beyond the periphery of the patch 92 and have freedom of movement with respect to the patch.

Outer extension members 108 are adhered or joined to the ends of the step member 106. The outer extension members 108 have skin-contacting surface and an outer surface that may be joined to the skin-contacting surface of the step member 106. The outer extension members 108 each have two ends that extend beyond the width of the step member 106. As shown in FIG. 12, the ends extend at equal distances beyond the width of the step member 106. Alternate constructions in which the ends extend from the step member at different distances are possible.

Inner extension member 110 has a skin-contacting surface and an outer surface. Inner extension member 110 is joined at its outer surface to the skin contacting surface of the step member 106. The inner extension member 110 is positioned along the length of the step member 106 such that it fits within the hole 94 formed through the patch 92. The inner extension member 110 has freedom of movement with respect to the patch 92. As shown in FIG. 12, inner extension member 110 has a generally rectangular shape in plan view, although other shapes are contemplated within the scope of this invention.

While the extension members are oriented generally perpendicular to the step member in FIG. 12, alternate orientations are permitted. For example, extension members may be engaged to the step members at angles within the range of 15 to 165 degrees, preferably from 45 to 135 degrees.

FIGS. 14 and 15 illustrate a seventh embodiment 120 of a vibration dampening device according to the present invention. The seventh embodiment 120 comprises a generally round patch 122 that has a skin-contacting surface and an outer surface. Although shown with a generally round shape in plan view in FIG. 14, alternate patch shapes are contemplated and within the scope of the invention. Dotted line 124 defines the boundary whereby adhesive 126 is applied to a central portion of the skin-contacting surface of the patch 122. Slits 128 are cut through the thickness of the patch 122 at its periphery to form wing sections at the peripheral edge of the patch 122. The wing sections have freedom of movement relative to the central portion of the patch to which adhesive is applied, and relative to adjacent wing sections.

Referring next to FIG. 16, an eighth embodiment 130 of a vibration dampening device according to the present invention is a patch 132 defining a skin-contacting surface, an outer surface and an outer periphery. The patch 132 further defines a central opening or hole 134 through the thickness thereof. The patch 132 comprises a generally round shape in plan view, and the hole 134 is a generally round circular hole that shares a common center with the patch 132. Alternate shapes for the patch, and alternate positioning of the hole are contemplated and within the scope of this invention.

Dotted lines 136, 138 define the boundaries between which adhesive is applied to the skin-contacting surface of the patch 132. A series of slits 140 are cut through the thickness of the patch 132 around the outer periphery to form wing members that have freedom of movement with respect to the central portion of the patch 132 that bears adhesive. As series of slits 142 are cut through the thickness of the patch 132 terminating at the central opening or hole 134 to form wing members that have freedom of movement with respect to the central portion of the patch 132 that bears adhesive.

The vibration dampening devices according to the invention may be used singly or in combination to dampen vibrations traveling along soft tissue and musculature in the region at or near the patch. FIG. 1 shows the back of a human figure having a patch 42 of the third embodiment 40 applied to the shoulder blade, and having a patch 122 of the seventh embodiment 120 applied to the back of the neck. FIG. 17 shows a human arm having a patch of the first or second embodiments 10, 20 applied to the wrist, and a patch of the seventh embodiment 120 applied to the forearm. The patches are applied to skin over muscles or joints subject to injury when subjected to vibrational forces. The elements, such as step members, extension member and wing sections of the vibration dampening devices, that have freedom of movement help to dampen vibrations from continuing to travel longitudinally along the soft tissue and musculature beyond the device In any embodiments of the invention, ends of the step members or wing sections or extensions were stated to have freedom of movement with respect to the patch. By "freedom to move" or "freedom of movement" is meant that an extending end of a step member or a wing section or extension may flexibly oscillate upwards and downwards or closer to and farther from the human body part or human skin to which the patch has been adhered. It is this relative freedom of movement of a distal end of a step member, or a wing section or an extension or other peripheral portion from the adhered portion of the patch that will apply a counter force to dampen vibrations based on Hooke's law ($F=k*x$) where k (force constant) is from 0.1 to 5 pounds/inch and x is the displacement distance moved by the end of a step member or wing section or extension.

A preferred thickness for the patch of the various embodiments is from 0.158 to 2.54 cm (1/16 to 1 inch), and most preferably is about 0.31 cm (1/8 inch). Thickness may vary depending upon body location for best form, fit and function. Preferably, the thickness of the step members 16, 18, 26, 28, 48, 66, 82, and 106 is in the range of 0.158 to 2.54 cm (1/16 to 1 inch), and most preferably is 0.317 cm (1/8 inch). Preferably, the thickness of the extension members 84, 108 and 110 is comparable to the thickness of the patch.

A preferred thickness for the patches of embodiments 120 and 130 is from 0.158 to 2.54 cm (1/16 to 1 inch), and most preferably is about 0.31 cm (1/8 inch), which includes the central portion of the patch as well as the wing members.

In any embodiments of the invention, when step members or extension members are attached to one another or to the patch material, preferably attachment is by an elastomeric adhesive that can stretch when subjected to tensile force without de-adhering. One adhesive that meets these conditions is a VELCRO® adhesive. Other adhesives are ALCOTE 532 or 555, available from Rohm and Haas Company, Philadelphia, Pa. Alternatively, step members and extension members may be attached by stitching with an elastomeric thread, or by fasteners such as buttons, grommets, rivets or staples.

Preferably, the patches are formed from a stretchable or viscoelastic material, such as neoprene, polyethylene, polyurethane or spandex. The patch material may be covered with a woven or nonwoven fabric. Suitable materials for the woven or nonwoven fabric or covering comprise nylon or rayon or DACRON® (trademark of E.I. DuPont de Nemours & Company) or GORE-TEX® (trademark of W. L. Gore & Associates). Other coverings include blends of synthetic and natural fibers, such as cotton, nylon, rayon blends. Particularly preferred materials for the patch are laminate structures having a viscoelastic material sandwiched between two woven fabric layers, such as polymer materials made by Rubberite, including R-1400-N, a neoprene polymer material that has an elongation of 200%, 4219-NEU, a neoprene polymer material that has an elongation of 130%, G231-N, a neoprene polymer material that has an elongation of 450%, SCE43B, a neoprene/EPDM/SBR polymer material that has an elongation of 150%, ENSOLITE IV2, a neoprene/PVC/Nitrile polymer material that has an elongation of 100%, and HYPUR-CE T0805, a polyurethane polymer material that has an elongation of 100%. One particularly preferred material, R1400-N, is a viscoelastic material sandwiched between two woven fabric or covering layers to form a laminate structure. This preferred material for the patch has a density in the range of 7 to 15 pounds per cubic foot, a tensile strength from 40 to 80 psi, a minimum elongation of 100%, and a compression deflection at 25% of from 3 to 10 psi.

Preferred stretchable or viscoelastic materials for forming the patch have the following properties as set forth in Table I:

TABLE I

| Physical property | Unit of Measure | Range |
| --- | --- | --- |
| Compression deflection @ 25% | psi | 3 to 10 |
| Density | Lbs/ft$^3$ | 7 to 15 |
| Tensile Strength | psi | 40 to 80 |
| Elongation (minimum to maximum) | % | 100 to 450 |
| Temperature range | °F. | −70 to +250 |
| Force constant (k = F/x) | Lbs/inch | 0.1 to 5.0 |

The force constant of a step member or extension member may be varied by using different material to construct the member, or by varying the thickness or shape of the outer periphery of the member. As one example, the force constant (k) of the material selected for step member 26 is from 0.5 to 2 lb/in$^2$, whereas the force constant (k) for the material selected for extension member 28 is from 2 to 3 lb/in$^2$, and that of the patch base 22 is from 3 to 5 lb/in$^2$. As another example, the force constant (k) of the material selected for step member 26 is from 0.5 to 2 lb/in$^2$, whereas the force constant (k) for the material selected for extension member 28 is from 2 to 5 lb/in$^2$.

Use of materials with different force constants for the step members, wings and/or extensions allows the vibration dampening device to better respond to vibrations having different frequencies and amplitudes. Alternatively, forming step members or extension members with nonuniform thickness can change dampening performance. For example, step member ends may be thicker than other portions.

The vibration dampening patches of the invention are passive mechanical vibration dampening devices. Vibrations in musculature and soft tissue generally have frequencies from less than 1 to about 500 cycles per second (Hz) and amplitudes from less than 1 mm (e.g., in muscular areas) to over 25 mm (e.g., in fatty soft tissue areas). Generally, as frequencies increase to over 2000 cycles per second, the amplitude of the vibrations will decrease. Under a shock event, vibration frequencies in tendons can range from 1 to over 2000 cycles per second (Hz). Tissue movement in both amplitude and frequency commonly leads to pain or injury. The patches counter radially traveling vibrations by supporting the skin and soft tissue in an area. The patches in combination with step members and/or wing sections best counter longitudinally traveling vibrations. When the longitudinal vibration meets the vibration dampening patch, the ends of the step members or the extension members, or the wing sections, or any combination thereof, may move freely to apply counter forces opposite to the vibration amplitude to help restore the skin and tissue to the pre-shocked position. That the ends of the step member (or wing sections) extending from the periphery of the patch may move freely is an important feature of these embodiments of the invention. Under Hooke's law, the restoring force F is calculated as $F=k^*x$, where k (force constant) is from 0.1 to 5 pounds/inch and x is the displacement distance moved by the end of the step member. The step members thus apply a restoring force to counter the longitudinal and/or radial vibration.

For example, if step member movement induced by vibration is translated to be linear movement (x) of 0.1 inch, and the k value for the wing material is 2 pounds/inch, then the restoring force F is calculated as 2 pounds/inch times 0.1 inch or 0.2 pounds-force. If the vibration dampening device has two ends of a step member extending from a patch, and if the step member ends have equivalent k value, the restoring force F is 2 times 0.2 pounds-force or 0.4 pounds-force. If the two step members having ends extend from both sides of the patch, such as shown in FIGS. 2 and 3, the restoring force F is doubled to 0.8 pounds-force.

If multiple step members each formed of a material with a different modulus of elasticity (and thus different force constant) are used in combination, a variety of restoring forces to counter longitudinal vibrations are applied. Under Hooke's law, within the elastic limit, deformation produced is proportional to the stress.

The invention has been illustrated by detailed description and examples of the preferred embodiments. Various changes in form and detail will be within the skill of persons skilled in the art. Therefore, the invention must be measured by the claims and not by the description of the examples or the preferred embodiments.

The invention claimed is:

1. A vibration dampening device for engaging to human skin, comprising: a patch having a nominal width and a nominal length and defines an outer periphery, and wherein said patch has a body contacting surface and an outer surface; and a step member engaged to the patch, wherein said step member (i) comprises a material having an elongation of at least 100%, (ii) has a distal end that extends beyond the outer periphery and (iii) has freedom of movement with respect to the patch, (iv) has a length and defines a center axis along its length, and (iv) comprises an extension member appended to the step member at a position along its length; and further wherein the patch defines a slot, and the step member is engaged to the patch by threading it through said slot, and further wherein the patch defines a central opening formed therethrough.

2. The device of claim 1, wherein the extension member is appended to the step member such that the extension member is held within the central opening formed through the patch.

3. The device of claim 2, further comprising a plurality of central openings formed through the patch, and a plurality of extension members appended to the step member such that said extension members are held within the central openings in a one to one relation.

4. The device of claim 2, wherein the extension member has length and width dimensions that are less than the dimensions of the central opening in the patch.

5. The device of claim 1, wherein the extension member defines a center axis along its length and said extension member is appended to the step member such that the center axis of the extension member is generally perpendicular to the center axis of the step member.

6. The device of claim 1, wherein the extension member has a body contacting surface and is formed to have a simple geometric shape selected from the group consisting of: square, rectangle, triangle, oval, and circle.

7. The device of claim 1, wherein the extension member is appended to the step member with adhesive.

8. The device of claim 1, wherein the step member is engaged with adhesive to the outer surface of the patch at selected points of contact.

9. A vibration dampening device for engaging to human skin, comprising: a patch having a nominal width and a nominal length and defines an outer periphery, and wherein said patch has a body contacting surface and an outer surface; and a step member engaged to the patch, wherein said step member (i) comprises a material having an elongation of at least 100%, (ii) has a distal end that extends beyond the outer periphery and (iii) has freedom of movement with respect to the patch, (iv) has a length and defines a center axis along it s length, and (iv) comprises an extension member appended to the step member; and further wherein the patch defines a slot, and the step member is engaged to the patch by threading it through said slot, said vibration dampening device further comprising one or more wings formed in the outer periphery of the patch, wherein the patch defines a central portion and the wings have freedom of movement with respect to the central portion.

10. The device of claim 9, wherein the wings are formed by slitting through a portion of the patch, wherein the patch defines a central portion and the slitting does not extend to said central portion.

11. The device of claim 10, wherein the wings are formed by a series of slits cut through the patch at a corner of the patch.

12. The device of claim 9, wherein an adhesive is applied on the body contacting surface at the central portion of the patch.

13. A vibration dampening device for engaging to human skin, comprising: a patch having a nominal width and a nominal length and defines an outer periphery, and wherein said patch has a body contacting surface and an outer surface; and a step member engaged to the patch, wherein said step member (i) comprises a material having an elongation of at least 100%, (ii) has a distal end that extends beyond the outer periphery and (iii) has freedom of movement with respect to the patch, (iv) has a length and defines a center axis along it s length, and (iv) comprises an extension member appended to the step member; and further wherein the patch defines a slot, and the step member is engaged to the patch by threading it through said slot, said vibration dampening device further comprising a second step member engaged to the patch, and wherein said second step member has a distal end that extends beyond the outer periphery, and further wherein the second step member is engaged by threading it between the outer surface of the patch and the step member.

14. The device of claim 13, wherein said second step member is adhered to the outer surface of the patch.

15. A vibration dampening device for engaging to human skin, comprising: a patch having a nominal width and a nominal length and defines an outer periphery, and wherein said patch has a body contacting surface and an outer surface; and a step member engaged to the patch, wherein said step member (i) comprises a material having an elongation of at least 100%, (ii) has a distal end that extends beyond the outer periphery and (iii) has freedom of movement with respect to the patch, (iv) has a length and defines a center axis along it s length, and (iv) comprises an extension member appended to the step member; and further wherein the patch defines a slot, and the step member is engaged to the patch by threading it through said slot, said vibration dampening device further comprising a second step member engaged to the patch, and wherein said second step member (a) has a distal end that extends beyond the outer periphery, and (b) defines a center axis along its length, and further wherein the step member and second step member are engaged to the patch such that the center axis of the step member and the center axis of the second step member are generally perpendicular to one another.

16. A method for dampening vibration of soft tissue or musculature of a human wearer's body part, comprising:
providing a vibration dampening device for engaging human skin in the form of a patch comprising a viscoelastic material, said patch having a nominal width and a nominal length and defining an outer periphery and a slot, and wherein said patch has (i) a body contacting surface comprising an adhesive and (ii) an outer surface, and wherein a step member and a second step member each with a distal end are engaged to the patch so that the distal end of the step member and second step member both extend beyond the outer periphery of the patch, said vibration dampening device further comprising a second step member engaged to the patch, and wherein said second step member has a distal end that extends beyond the outer periphery, and further wherein the step member defines a center axis along its length and wherein the second step member defines a center axis along its length, and further wherein the step member and second step member are engaged to the patch such that the center axis of the step member and the center axis of the second step member are generally perpendicular to one another; and
removably engaging the device to the body part.

17. A method for dampening vibration of soft tissue or musculature of a human wearer's body part, comprising:
providing a vibration dampening device for engaging human skin in the form of a patch comprising a viscoelastic material, said patch having a nominal width and a nominal length and defining an outer periphery and a slot, and wherein said patch has (i) a body contacting surface comprising an adhesive and (ii) an outer surface, and wherein a step member and a second step member each with a distal end are engaged to the patch so that the distal end of the step member and second step member both extend beyond the outer periphery of the patch, said vibration dampening device further comprising one or more wings formed in the outer periphery of the patch, wherein the wings have freedom of movement with respect to a central portion of the patch; and removably engaging the device to the body part.

18. A method for dampening vibration of soft tissue or musculature of a human wearer's body part, comprising:

providing a vibration dampening device for engaging human skin in the form of a patch comprising a viscoelastic material, said patch having a nominal width and a nominal length and defining an outer periphery and a slot, and wherein said patch has (i) a body contacting surface comprising an adhesive and (ii) an outer surface, and wherein a step member and a second step member each with a distal end are engaged to the patch so that the distal end of the step member and second step member both extend beyond the outer periphery of the patch, and further wherein the step member has a length and a width and defines a center axis along its length, and wherein the patch defines a central opening formed therethrough, and further comprising an extension appended to the step member at a position along its length; and removably engaging the device to the body part.

19. The method of claim 18, wherein the extension is appended to the step member such that the extension is held within the central opening formed through the patch.

* * * * *